United States Patent [19]

Suzuki et al.

[11] 4,039,384

[45] Aug. 2, 1977

[54] CREATININE AMIDOHYDROLASE AND CREATINE AMIDINOHYDROLASE AND PROCESS FOR PRODUCING THEM

[75] Inventors: Masaru Suzuki, Kashiwa; Narimasa Saito, Noda, both of Japan

[73] Assignee: Noda Institute for Scientific Research, Noda, Japan

[21] Appl. No.: 669,757

[22] Filed: Mar. 24, 1976

[30] Foreign Application Priority Data

Apr. 5, 1975 Japan .................................. 50-40792
Apr. 5, 1975 Japan .................................. 50-40793

[51] Int. Cl.$^2$ ...................... C12D 13/10; C07G 7/02; C12K 1/00

[52] U.S. Cl. ........................................ 195/62; 195/65; 195/66 R

[58] Field of Search .................... 195/62, 65, 66 R

[56] References Cited

U.S. PATENT DOCUMENTS

| 3,806,419 | 4/1974 | Mollering et al. ........... 195/62 |
| 3,806,420 | 4/1974 | Holz et al. ............... 195/66 R |

*Primary Examiner*—Lionel M. Shapiro
*Attorney, Agent, or Firm*—Schuyler, Birch, Swindler, McKie & Beckett

[57] ABSTRACT

Creatinine amidohydrolase and creatine amidinohydrolase can be obtained by culturing a strain belonging to Genus Flavobacterium, Genus Micrococcus or Genus Corynebacterium and having an ability to produce creatinine amidohydrolase and creatine amidinohydrolase in the presence of creatinine, creatine or a mixture thereof and separating creatinine amidohydrolase and creatine amidinohydrolase from the cultured fluid.

16 Claims, 2 Drawing Figures

CREATININE AMIDOHYDROLASE AND CREATINE AMIDINOHYDROLASE AND PROCESS FOR PRODUCING THEM

This invention relates to novel enzymes, creatinine amidohydrolase and creatine amidinohydrolase, and to a process for producing them. More particularly, it relates to a process for producing creatinine amidohydrolase and creatine amidinohoydrolase with high efficiency by use of a strain belonging to the Genus Flavobacterium, Genus Micrococcus or Genus Corynebacterium and having an ability to produce creatinine amidohydrolase and creatine amidinohydrolase.

Creatinine amidohydrolase is an enzyme which participates as a catalyst in the following reaction:

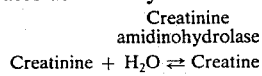

Creatinine + H$_2$O ⇌ Creatine

On the other hand, creatine amidinohydrolase is an enzyme which hydrolyzes creatine into urea and sarcosine, of which reaction is represented by the following equation:

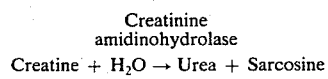

Creatine + H$_2$O → Urea + Sarcosine

Figure 1:
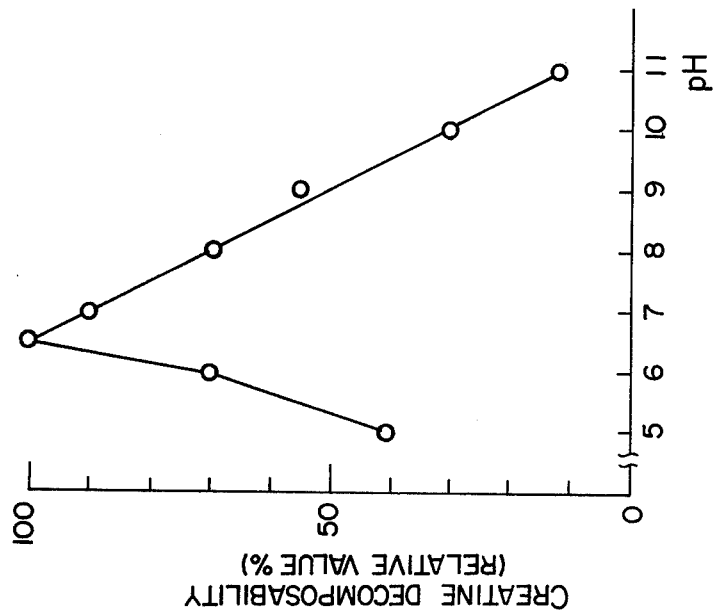
Figure 2:
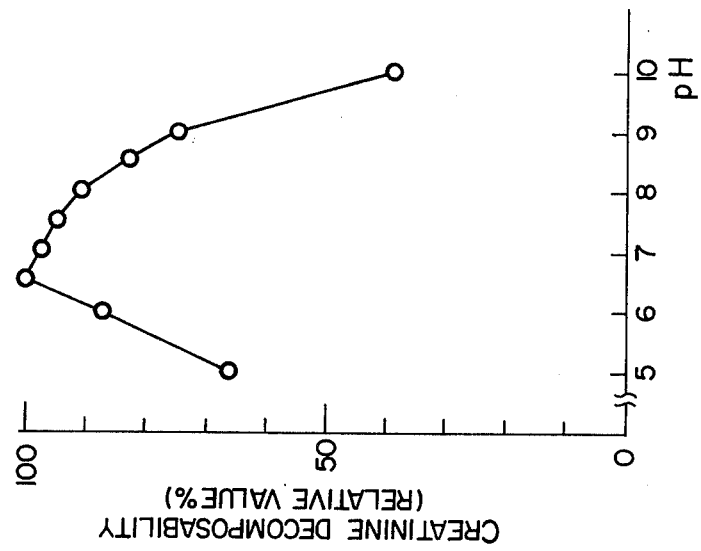

In the accompanying drawings, FIG. 1 illustrates the optimum pH range for creatinine amidohydrolase prepared according to this invention as measured in the presence of creatinine as a substrate. FIG. 2 illustrates the optimum pH range for creatinine amidohydrolase prepared according to this invention as measured in the presence of creatine as a substrate.

At present, in the field of clinical medicine, the functional diagnosis of kidney is carried out by determining creatinine present in serum and urine. The determination is usually based on the nonenzymatic Jaffe reaction. However, the reaction is nonspecific and the result is poor in reliability because of the great experimental error. Thus, it is desired to develop a method for the enzymatic determination based on creatinine-decomposing enzyme. On the other hand, the determination of creatine present in serum and urine is applicable to the diagnosis of muscular or renal diseases.

At the present time, the determination of creatine is usually carried out by analyzing creatinine by means of Jaffe reaction on the basis of the characteristic property of creatine that creatine undergoes dehydration to give creatinine when heated in an acidic medium.

The above-mentioned method of determining creatine is disadvantageous in that Jaffe reaction is nonspecific and said serum and urine contain a large quantity of other substances which make the experimental result erroneous and thereby reduce the reliability of the measurement. Thus, it is desired to develop a method for the enzymatic determination of creatine by utilization of an enzyme which can decompose creatine specifically.

It has hitherto been known that enzymes capable of decomposing creatinine are present in the microorganisms belonging to the Genus Pseudomonas [Biochim and Biophys Acta, Vol. 6, p. 210 (1950)], Genus Arthrobacter [Molecular and Cellular Biochemistry, Vol. 3, p. 9, (1974)], and Genus Alcaligenes (U.S. Pat. Nos. 3,806,416 and 3,806,420).

On the other hand, enzymes capable of decomposing creatine are known to be present in the microorganisms belonging to the Genus Pseudomonas [Journal of General Microbiology, Vol. 14, p. 351 (1956)], Genus Arthrobacter (Molecular and Cellular Biochemistry, Vol. 3, p. 9, 1974) and Genus Alcaligenes (U.S. Pat. Nos. 3,806,416 and 3,806,420).

However, all the creatinine- or creatine- decomposing enzymes obtained from the above-mentioned microorganisms are disadvantageous in that they are generally labile to the environmental conditions such as temperature, pH, oxygen and the like and that they are all found in microorganisms so that their collection necessitates a two-step procedure comprising, on one hand, a step for increasing and culturing microorganisms and, on the other hand, a step for collecting the cultured bacteria and extracting the enzymes from the cells by means of grinding, chemical or enzymatic digestion, which makes the purification process quite complicated and reduces the product yield.

In view of above, the inventors searched for the strain capable of producing creatinine amidohydrolase and creatine amidinohydrolase with high yields extensively in the microbial world. As a result, it was discovered that the cultivation of microorganims, the inductive production of enzyme and the accumulation of enzymes in the culture solution can be achieved simultaneously and, therefore, creatinine amidohydrolase and creatine amidinohydrolase can be produced in high yields in only one step without extracting the enzymes from the cultured cells by culturing a strain belonging to the Genus Flavobacterium, Genus Micrococcus or Genus Corynebacterium in the presence of creatinine, creatine or a mixture thereof. Based on this finding, the present invention has been accomplished.

An object of this invention is to provide novel creatinine amidohydrolase and creatine amidinohydrolase and a novel process for producing them.

Other objects and advantages of this invention will be apparent from the descriptions below.

The above-mentioned object of the invention can be achieved by culturing a strain belonging to the Genus Flavobacterium, Genus Micrococcus or Genus Corynebacterium and having an ability to produce creatinine amidohydrolase and creatine amidinohydrolase in the presence of creatinine, creatine or a mixture thereof and collecting creatinine amidohydrolase and creatine amidinohydrolase from the culture fluid.

To separate the above-mentioned two enzymes, a mixture thereof is loaded on a DEAE-cellulose column previously equilibrated with 0.05 M of phosphate buffer (pH 8.0), whereby creatinine amidohydrolase is adsorbed on the column and creatine amidinohydrolase is passed therethrough and obtained in a unadsorbed portion. Alternatively, both enzymes are adsorbed on a DEAE-Sephadex A-50 column equilibrated with the above-mentioned buffer, and creatine amidinohydrolase is firstly eluted, and then creatine amidohydrolase is eluted with a linear gradient of NaCl, respectively.

The detail of this invention will be explained below.

The strain used in this invention may be any of the strains so far as they belong to the Genus Flavobacterium, Genus Micrococcus or Genus Corynebacterium and have an ability to produce creatinine amidohyrolase and creatine amidinohydrolase. Varieties or mutants of the above-mentioned strains may also be used.

Concrete examples of said strains belonging to the Genus Flavobacterium include Flavobacterium U-188 (ATCC 31200, FERM-P No. 2922) and the like. Concrete examples of said strains belonging to the Genus Micrococcus include *Micrococcus luteous* ATCC No. 398 and the like. Concrete examples of said strains belonging to the Genus Corynebacterium include Corynebacterium U-41 (ATCC 31201, FERM-P No. 2923) and the like.

Flavobacterium U-188, referred to above, (hereinafter called Strain U-188) is a strain that the inventors have newly discovered in a humus soil. Its bacteriological properties are as mentioned below. The description of bacteriological properties is made in accordance with the manner of "Manual of Microbiological Methods" (published in 1957 by McGraw-Hill Book Company, Inc.). The same holds in the cases of other strains.

a. Morphology

Microscopic observation (cultured in a bouillon-agar medium at 30° C for 48 hours)

1. Shape and size of cell: A rod having a size of 0.5 – 0.7 x 1.5 – 1.7 micron.
2. Polymorphism of the cell: There is observed no polymorphism depending on the life cycle, and the cells occuring singly and in dual.
3. Motility: Motile by means of 3 to 7 by peritrichous flagella.
4. Spore: It forms no spore.
5. Gram-stain: Negative
6. Acid-fast: Negative.

b. The State of Growth in Various Broth:

1. Boulillon-agar plate culture (2 days at 30° C) Circular colonies are uneven, convex, repand, faint ocher; 2 to 3 mm in diameter.
2. Bouillon-agar slant culture (2 days at 30° C) Growth well, spreading, dim glistening producing water-insoluble yellow-brown pigment.
3. Bouillon submerged culture (1 day at 30° C) Membranous pellicle with heavy sediment.
4. Bouillon-gelatine stab culture (1 to 40 days at 20° C)

Growth well on the surface and in the upper layer. No liquefaction.

5. Litmus milk (1 to 14 days at 30° C) Unchanged (pH 6.8) No reduction of litmus, nor coagulation, nor peptonization.
6. Potato culture (2 days at 30° C) No visible growth.

c. Physiological properties

1. Reduction of nitrates: Intensely observed.
2. Denitrification reaction: Not observed.
3. MR test: Negative.
4. VP test: Negative.
5. Formation of indole: Not observed.
6. Formation of hydrogen sulfide: Not observed.
7. Hydrolysis of starch: Not observed.
8. Utilization of citric acid: Not observed. (Koser- and Cristenen-medium are used in combination).
9. Inorganic nitrogen source: Not utilized (Ammonium salts, nitrates).
10. Formation of pigment: A water-insoluble, ocher colored pigment is formed.
11. Urease: Not formed.
12. Oxydase: Formed.
13. Catalase: Formed.
14. Growing condition range Optimum conditions of the growth: 25° – 35° C, pH 7 – 9, aerobic.

Conditions permitting the growth: It can grow under an aerobic to slightly facultatively anaerobic condition at temperature between 5° and 40° C, though it hardly grows at 50° C (bouillon shaking culture). The pH range permitting the growth is 6 to 11. When heated at 80° C for 30 minutes it becomes extinct.

15. Behavior to oxygen: Aerobic.
16. O-F test (by Hugh Leifson method): Negative.
17. Coagulation of milk: It does not coagulate milk.
18. Utilization of carbon sources: Neither acid nor gas is formed from carbon sources such as L-arabinose, D-glucose, D-mannose, D-fructose, D-galactose, maltose, sucrose, lactose, trehalose, D-sorbital, D-mannitol, inositol, glycerine, starch, raffinose, dextrin, inulin, glycogen, cellulose and the like.

Physiological Characteristics

Strain U-188 has a high activity for producing creatinine amidohydrolase and creatine amidinohydrolase simultaneously and inductively in the presence of creatinine and/or creatine. With the lapse of time for culturing, urea is formed and accumulated in the culture solution. The medium becomes alkaline to generate ammonia. The production of the enzymes and the formation of urea and ammonia are not observed in the usual nutrient medium containing no creatinine nor creatine.

By comparing the above-mentioned characteristic properties of Strain U-188 with the classification mentioned in "Bergey's Mannual of Determinative Bacteriology, 8th Ed. (1974) ", a judgement can be made that Strain U-188 belongs to the Genus Flavobacterium. Respecting species, however, it is found that Strain U-188 does not correspond to any of the known bacterial species. Thus, Strain U-188 can be considered to be a new bacterial species for the following reasons.

Strain U-188 is a gram-negative, aerobic, non sporforming rod-shaped bacteria forming an ocher colored pigment (water-soluble) in the usual nutrient medium. Motile by means of peritrichous flagella. In addition, it produces neither acid nor gas from carbon sources and does not change litmus milk. Therefore, it belongs to the Genus Flavobacterium. It is regarded as analogous to *Flavobacterium rigense* in that it is isolated not from sea water but from soil, that is is motile and well grows at 37° C, that it requires no NaCl and that is reduces nitrates into nitrites.

As shown in Table 1, however, it belongs to a different species from *Flavobacterium rigense* in that the pigment produced by Strain U-188 has an ocher color independently of the culture conditions and is water-insoluble, that is does not liquefy gelatine, that it forms neither acid nor gas from glucose and other carbon sources, and that it does not grow on potato.

Table 1

| Item | Kind of Strain | *Flavobacterium* U-188 | *Flavorbacterium Rigense* |
|---|---|---|---|
| 1. | Formation of pigment | Ocher (water-insoluble) | Initially yellow which later turns to orange (soluble) |
| 2. | Growth at 37° C | Good | Good |
| 3. | Liquefaction of gelatine | Not observed | Infundibuliform liquefaction |
| 4. | Peptonization of casein | Not observed | Not observed |
| 5. | Utilization of sugar (formation of acid) | | |
| | Glucose | Not observed | Observed |
| | Sucrose | Not observed | Unknown |
| | Maltose | Not observed | Unknown |
| 6. | Formation of hydrogen sulfide | Observed | Not observed |
| 7. | Reduction of Nitrates | Observed | Observed |

Table 1-continued

| Item | Kind of Strain | Flavobacterium U-188 | Flavorbacterium Rigense |
|---|---|---|---|
| 8. | Growth on potato | Not observed | Good |

Flavobacterium U-188 is deposited in Fermentation Research Institute, Agency of Industrial Science and Technology, Chiba, Japan as FERM-P No. 2922 and in American Type Culture Collection (U.S.A) as ATCC 31200.

Next, Corynebacterium U-41 (hereinafter referred to as Strain U-41) is a strain which has been newly discovered in a humus soil by the present inventors. Its bacteriological properties are as mentioned below.

a. Morphology

Microscopic observation (cultured in a bouillon-agar medium at 30° C for 6 hours)
1. Shape and size of cell: Short rod having a size of 0.3 - 0.5 × 1.0 - 1.3 micron.
2. Polymorphism of the cell: There is observed a polymorphism depending of the life cycle.
3. Motility: Non-motile.
4. Spore: None.
5. Gram-stain: Positive.
6. Acid-fast: Negative.

b. State of Growth in Various Mediums

1. Bouillon-agar plate culture (2 days at 30 ° C) Circular colonies are entire, smooth, dim yellow color; 2 mm in diameter.
2. Bouillon-agar slant culture (2 days at 30° C) Growth well, filiform producing water-insoluble, dim yellow pigment.
3. Bouillon submerged culture (2 days at 30° C) Flagile pellicle with rim.
4. Bouillon-gelatine stab culture (1 - 40 days at 20° C) Infundibuliform liquefaction.
5. Litmus milk (1 - 14 days at 30° C) Reduction of litmus to red (pH 7.9). No coagulation but peptonization.

c. Physiological Properties

1. Reduction of nitrates: Observed.
2. Denitrification: Not observed.
3. MR test: Negative.
4. VP test: Negative.
5. Formation of indole: Not observed.
6. Formation of hydrogen sulfide: Observed.
7. Hydrolysis of starch: Observed.
8. Utilization of citric acid: Observed (Koser- and Christensen-medium are used in combination).
9. Inorganic nitrogen source: Not utilized (ammonium salts, nitrates).
10. Formation of pigment: A water-insoluble, faintly yellow colored pigment is formed.
11. Urease: Not formed.
12. Oxydase: Formed.
13. Catalase: Formed.
14. Growing condition range Optimum conditions for the growth: 25° - 35° C, pH 6 - 9, aerobic.

Conditions permitting the growth: It can grow under an aerobic to slightly facultatively anaerobic condition at temperature between 5° and 40° C but it hardly grows at 45° C (bouillon shaking culture). The pH range permitting the growth is 6 - 11. When heated at 80° C for 30 minutes it becomes extinct.

15. Behavior to oxygen: aerobic.
16. O-F test (Hugh Leifson method): Negative.
17. Coagulation of milk: Not observed.
18. Utilization of carbon sources: Neither acid nor gas is formed from carbon sources such as L-arabinose. D-glucose, D-mannose, D-fructose, D-galactose, maltose, sucrose, lactose, trehalose, D-sorbitol, D-mannitol, inositol, glycerine, starch, raffinose, dextrin, inulin, glycogen, cellulose and the like.

Physiological Characteristics

Strain U-41 has a high activity for producing creatinine amidohydrolase and creatine amidinohydrolase simultaneously and inductively in the presence of creatinine and/or creatine. With the lapse of time for culturing, urea is formed and accumulated in the culture solution. The medium becomes alkaline to generate ammonia. The production of the enzymes and the formation of urea and ammonia are not observed in the usual nutrient medium containing no creatinine nor creatine.

By comparing the above-mentioned characteristic properties of Strain U-41 with the classification mentioned in "Bergey's Mannual of Determinative Bacteriology, 7th Ed. (1957) and 8th Ed. (1974)", a judgement can be made that Strain U-41 belongs to the Genus Corynebacterium. Respecting species, however, it is found that Strain U-41 does not correspond to any of the known bacterial species. Thus, Strain U-41 can be considered to be a new bacterial species for the following reasons.

Strain U-41 is regarded as belonging to the Genus Corynebacterium for the reasons that it exhibits polymorphism depending upon the life cycle, that the gram-stain is always positive and by no means negative, that it is a non sporforming rod-shaped bacteria and grows in the usual nutrient medium, that it cannot grow at a temperature above 50° C and therefore it has no heat resistance, and that it has no ability to decompose cellulose.

It is regarded as analogous to Corynebacterium rathayi in that it is not isolated from animal origin, that it reduces nitrates into nitrites and that it liquiefies gelatine. However, Strain U-41 is isolated from soil, is not a pathogenic bacterium for vegetables and, in addition, intensely liquefies gelatine and does not utilize carbon sources as shown in Table 2. That is, it is greatly different from Corynebacterium rathayi, so that it is judged to belong to a new species.

Corynebacterium U-41 is deposited in Fermentation Research Institute, Agency of Industrial Science and Technology, Chiba, Japan as FERM-P 2923 and in American Type Culture Collection as ATCC 31201.

Table 2

| Item | Kind of Strain | Corynebacterium U-41 | Coryhebacterium rathayit |
|---|---|---|---|
| 1. | Ability to liquefy gelatine | Strong | Mild and slow |
| 2. | Growth in nutrient medium | Good | Good |
| 3. | Utilization of sugar (formation of acid) | | |
| | Glucose | — | + |
| | Lactose | — | + |
| | Sucrose | — | + |
| 4. | Utilization of citric acid | Observed | Not observed |

Next, *Micrococcus luteus* ATCC 398, mentioned afore, is referred to in G. J. Hucker 426, Intern. Bull. Bacteriol. Nomen. and Taxon 2(3): 88(1952). It is deposited in ATCC (American Type Culture Collection) and now freely available [The American Type Culture Collection, Catalogue of Strains 8th Ed. (1968) p. 31].

In producing creatinine amidohydrolase and creatine amidinohydrolase by use of the above-mentioned strains, conventional solid culture may be employed. It is more preferable, however, to employ liquid culture.

The culture medium used in the present invention is so composed that one or more kind of nitrogen source, such as yeast extract, peptone, meat extract, corn steep liquor or water extract of soy bean or of wheat bran, is incorporated with one or more kind or inorganic salt, such as potassium primary phosphate, potassium secondary phosphate, magnesium sulfate, magnesium chloride, ferric chloride, ferric sulfate or manganese sulfate, and if necessary further with a sugar such as starch, vitamins and the like, appropriately.

In this invention, the above-mentioned strain is cultured in the presence of creatinine, creatine or a mixture thereof. The culture may be carried out, for example, by inoculating said strain into the above-mentioned medium which has preliminarily been incorporated with creatinine, creatine or a mixture thereof. Alternatively, it may also be carried out by adding creatinine, creatine or a mixture thereof to the culture within 5 hours after the culture is started, namely the strain is inoculated into the medium.

Quantity of said creatinine, creatine or a mixture thereof to be added to the above-mentioned culture medium is in the range of 0.01 to 5.0% (W/V), preferably in the range of 0.1 to 1.0% (W/V), based on the total weight of the medium.

It is advisable to adjust the initial pH value of medium to 7 - 9. The culture is carried out in an aerobic condition by means of an aeration-agitation submerged culture or by means of a shaking culture at temperature between 25° and 37° C, preferably about 30° C, for a time period of 10 to 48 hours, preferably 15 to 36 hours. The above-mentioned strains can afford to produce and accumulate a large quantity of creatinine amidohydrolase and creatine amidino-hydrolase in the culture solution with a high efficiency by one-step culture.

In collecting creatinine amidohydrolase or creatine amidinohydrolase from the cultured broth after the completion of the culture according to the invention, the conventional means for collecting enzymes may be adopted.

Since the considered enzymes are present in the liberated form in the culture solution, a crude liquor containing the enzymes can be obtained by removing the cells and insoluble materials from the culture solution. The crude liquor can be put to use either directly or after being prepared into a crude enzyme powder by means of lyophilization.

If one wishes to extract the creatinine amidohydrolase or creatine amidinohydrolase yet remaining in the microorganisms in a small amount, they are extracted after the cells are ground in the usual way or by means of an enzymatic digestion. Alternatively, the cells are submitted to autolysis by shaking or allowing to stand in the presence of toluene or the like to liberate the enzymes, after which the solution is separated from the solid matter by means of filtration or centrifugation, and if necessary it is made free from nucleic acid by a treatment with streptomycin sulfate, protamin sulfate or manganese sulfate, and then it is fractionated by adding ammonium sulfate, alcohol or acetone, the resulting precipitate is collected, the latter is dialyzed against water, and finally it is dried under vacuum to give crude enzyme powder.

The crude enzyme preparation thus obtained contains both the enzymes creatinine amidohydrolase and creatine amidinohydrolase. Creatinine amidohydrolase and creatine amidinohydrolase are isolated and purified from the crude enzyme preparation either by the adsorption-elution method by means of ion exchanger such as DEAE-cellulose (diethylaminoethylcellulose, manufactured by Brown, Co., U.S.A.), DEAE-Sephadex A-50 (diethylaminoethyl-Sephadex A-50, manufactured by Pharmacia Co., Sweden), QAE-Sephadex A-50 (manufactured by Pharmacia Co., Sweden) or the like; or by appropriately combining some of the gel-filtration method by means of Sephadex G-100, G-200 (manufactured by Pharmacia Co., Sweden) or Sepharose 6B (manufactured by Pharmacia Co., Sweden), the adsorption-elution method by means of hydroxyl appatite (Biogel HT, manufactured by Biolad Co., U.S.A.) and the electrophoresis method by means of polyacrylamide gel, and the like. Thus, highly purified enzymes can be obtained.

The physical and chemical properties of the pure creatinine amidohydrolase and creatine amidinohydrolase obtained by the above-mentioned purification are mentioned below:

I. creatinine amidohydrolase

1. The action and substrate specificity

This enzyme participates, as a catalyst, in the reversible reaction in which it hydrolyzes creatinine into creatine and, at the same time, it converts creatine into creatinine. $K_m$ value (Michaelis constant) of this enzyme for creatinine is $3.45 \times 10^{-2}$ mole (37° C, pH 6.5), while its $K_m$ for creatine is $4.35 \times 10^{-2}$ mole (37° C, ph 6.5). When this enzymatic reaction has reached the equilibrium, the concentration ratio between creatinine and creatine, namely the equilibrium constant, is represented by:

$$[\text{Creatine}]/[\text{Creatinine}] = 1.5 \ (37° \text{C, pH } 6.5)$$

2. Optimum pH and stable pH range

When creatinine is the substrate, optimum pH value is 6.5 as shown in FIG. 1. When creatine is the substrate, optimum pH value is similarly 6.5 as shown in FIG. 2. The stable pH range is 7.0 - 9.5.

3. Method for measuring the enzymatic activity

To 0.8 ml of 0.1 M creatinine solution are added 0.1 ml of 0.3 M phosphate buffer (pH 6.5) and 0.1 ml of a solution of this enzyme having an appropriate concentration, and the resulting mixture is allowed to react at 37° C for 10 minutes. The reaction is stopped by adding 2 ml of 2% sodium carbonate solution containing $10^{-3}$ M of P-CMB (p-chloromercurybenzoic acid). 0.1 ml of the reaction mixture is taken out, and is thoroughly mixed with 0.9 ml of distilled water, 0.5 ml of 2% α-naphthol solution in 99.5% ethanol, 0.5 ml of a mixture of 1.2% sodium hydroxide solution and 3.2% sodium carbonate solution and 0.5 ml of 0.05% diacetyl solution. The resulting mixture is allowed to stand at 25° C for 1 hour and then diluted with 2.5 ml of distilled water. Its absorbance (O. D. value) at 525 mµ is measured with photoelectric colorimeter. Quantity of the formed creatine is estimated by reference to a preliminarily prepared calibration curve. The quantity of enzyme necessary for producing 1 micromole creatine per 1 minute at 37° C is taken as one unit. (Normal reaction).

On the other hand, 0.1 ml of 0.3 M phosphate buffer (pH 6.5) and 0.1 ml of a solution of this enzyme having an appropriate concentration are added to 0.8 ml of 0.1 M creatine solution, and the resulting mixture is allowed to react at 37° C for 10 minutes. 0.1 ml of the reaction mixture is taken out, thoroughly shaken with a mixture comprising 0.9 ml of water, 1 ml of 1 N NaOH and 1 ml of 1% picric acid solution, and allowed to stand at 25° C for 20 minutes. Its absorbance at 520 m$\mu$ (O. D. value) is measured with photoelectric colorimeter. Quantity of the formed creatinine is estimated by reference to a preliminarily prepared calibration curve. The quantity of enzyme necessary for forming 1 micromole creatinine per 1 minute at 37° C is taken as one unit (Reverse reaction).

4. The range of optimum temperature

It is in the range of 40°– 70° C. A temperature of about 65° C is particularly preferable.

5. Thermal and pH stability

It can be kept stable at 45° C for 10 minutes. It completely loses its activity at 67° C in 10 minutes. It loses its activity at a pH value below 4 or above 12.

6. Inhibition, activation and stabilization

It is inhibited by p-CMB and mercury chloride. It is stabilized by glutathione (reduced form), L-Cysteine hydrochloride, and 2-mercaptoethanol.

7. Method of purification

Nucleic acid and bacteria are eliminated from the cultured broth by adding manganese sulfate and Hyflow-Super Cel to the latter and filtering the resulting mixture. The filtrate is dialyzed against 0.05 M phosphate buffer (pH 8.0) containing 1 milli-mole of 2-mercaptoethanol (hereinafter called as buffer A), after which the dialyzed solution is loaded on a DEAE-cellulose column previously equilibrated with buffer A. In this case, creatinine amidohydrolase is absorbed, while creatine amidinohydrolase is not adsorbed. The adsorbed enzyme is eluted with a linear gradient of NaCl from 0 to 0.5 M. The eluate is dialyzed against buffer A, after which it is adsorbed to a DEAE-Sephadex A-50 column previously equilibrated with buffer A and then eluted with a linear gradient of NaCl from 0 to 0.5 M. Thus, the enzyme is eluted out at a NaCl concentration of 0.2 to 0.3 M.

Subsequently, the eluate is concentrated, passed through a Sepharose 6B column, and eluted with buffer A. The fractions having the enzymatic acitivity are collected. They are concentrated and lyophilized to give a purified powder of the enzyme.

8. Molecular weight

The molecular weight of this enzyme is determined by gel filtration of Sephadex G-200 (manufactured by Pharmacia Co., Sweden) according to Andrew's method [P. Andrews, Biochem. J., 96, 595 (1965)]. Thus, the molecular weight is found to be about 150,000. The column is equilibrated with 0.05 M phosphate buffer (pH 8.0) containing 0.1 M NaCl and 1 millimole 2-mercaptoethanol, and the elution is carried out at 5° C.

On the contrary, creatinine amidohydrolase which has already been reported in prior arts, for example, U.S. Pat. Nos. 3,806,416 and 3,806,420 as mentioned previously, has the following physical and chemical properites:

Equilibrium constant: 1.27 (37° C, pH 8.0)
$K_m$ value for creatinine: $3.3 \times 10^{-2}$ M (37° C, pH 8.0)
Optimum pH: 8.0

As mentioned above, in the light of its emzymological and physico-chemical properties, this enzyme is considered a new creatinine amidohydrolase dissimilar to any of the known creatinine amidohydrolases.

II. Creatine amidinohydrolase

1. Action and substrate specificity

This enzyme has an ability to hydrolyze creatine into urea and sarcosine. $K_m$ (Michaelis constant) for creatine is $4.0 \times 10^{-2}$ mole (37° C, pH 7.7). It exerts no action upon creatinine. (2) Optimum pH and stable pH range Optimum pH is 7.7 and the stable pH range is 5.0 – 9.0.

3. Method for measuring enzymtic activity

To 0.8 ml of 0.1 M creatine solution are added 0.1 of 0.3 M phosphate buffer (pH 7.7) and 0.1 ml of a solution of this enzyme having an appropriate concentration, and the resulting mixture is reacted at 37° C for 10 minutes. Then, 2 ml of 2% (W/V) p-dimethylaminobenzaldehyde solution (prepared by dissolving 2 g of p-dimethylaminobenzaldehyde into 100 ml of 99.5% ethanol, adding 15 ml of concentrated hydrochloric acid and diluting the mixture with distilled water to a 2 times greater quantity) is added, and the resulting mixture is allowed to stand at 25° C for 30 minutes. Then, its absorbance (O. D. value) at 435 m$\mu$ is measured with photoelectric colorimeter. Quantity of the formed urea is estimated by reference to a calibration curve for urea which has been preliminarily prepared. The quantity of enzyme necessary for producing 1 micromole of urea per one minute at 37° C is taken as one unit.

4. The range of optimum temperature

It is in the range of 20°– 45° C. A temperature of about 37° C is particularly preferred.

5. Thermal and pH stability

It loses the activity at a pH value above 10. It loses its activity completely at 50° C in 10 minutes.

6. Inhibition, activation and stabilization

It is inhibited by p-CMB and mercury chloride. It is stabilized by glutathione (reduced form), L-cysteine hydrochloride and 2-mercaptoethanol.

7. Method of purification

Nucleic acid and bacteria are eliminated from the cultured fluid by adding manganese sulfate and Hyflow Super Cel and filtering the resulting mixture. The filtrate is dialyzed against buffer A after which the dialyzed solution is loaded on a column packed with DEAE-cellulose preliminarily equilibrated with buffer A. In this case, the adsorbed enzyme has an activity of creatinine amidohydrolase. The unadsorbed enzyme having an activity of creatine amidinohydrolase is adsorbed to DEAE-Sephadex A-50 preliminarily equilibrated with the above-mentioned buffer A and then eluted with a linear gradient of NaCl from 0 to 0.5 M, whereby the enzyme is eluted at a NaCl concentration of 0.1 – 0.3 M. Then, the eluate is concentrated, passed through a column of Sepharose 6B, and eluted with buffer A to collect the fraction having the activity of the enzyme. The fraction is concentrated and lyophilized to give a purified powder of the enzyme.

8. Molecular weight

The molecular weight of this enzyme is determined by gel filtration of Sephadex G-200 (manufactured by Pharmacia Co., Sweden) according to Andrews' method [P. Andrews, Biochem. J., 96, 595 (1965)]. It is found to be about 60,000. The column is equilibrated with 0.05 M phosphate buffer (ph 8.0) containing 0.1 M NaCl and 1 millimole 2-mercaptoethanol, and the elution is carried out at 5° C.

On the contrary, creatine amidinohydrolases which have already been reported in prior arts, for example (i) Journal of General Microbiology, Vol. 14, pp. 351 to 365 (1956) and (ii) U.S. Pat. Nos. 3,806,416 and 3,806,420 as mentioned previously, have the following physical and chemical properties:

$K_m$ value for creatine: i. $2.3 \times 10^{-2}$ M (30° C, pH 7.8)
ii. $5.0 \times 10^{-2}$ M (25° C, pH 7.6)
Relative activity for creatine: i. About 0.1 unit/mg-protein
Optimum temperature: i. 30° C
Optimum pH: i. 7.8 ii. 7.6

Further, an effect of inhibitors on creatine amidinohydrolase reported in the prior art are compared with those of this invention below:

| Inhibitor | Final concentration of inhibitor (M) | Percentage inhibition of creatine removal (%) | |
|---|---|---|---|
| | | This invention | Prior art (i) |
| Borate (pH 9.1) | $5 \times 10^{-2}$ | 40 | 80 |
| Azide | $2 \times 10^{-2}$ | 0 | 18 |
| Iodoacetate | $10^{-2}$ | 0 | 20 |

As mentioned above, in the light of its enzymological and physico-chemical properties, this enzyme if considered a new creatine amidinohydrolase dissimilar to any of the known creatine amidinohydrolases.

Thus, according to this invention creatinine amidohydrolase and creatine amidinhohydrolase having high purities can readily be obtained in a short period of time in a high yield.

The following examples will further concretely illustrate this invention but are not to be considered limitations thereupon. The unit of enzyme activity, referred to in the examples, is that concerning the normal reaction in the presence of creatinine or creatine as a substrate.

EXAMPLE 1

1 liter of a nutrient medium (pH 7.6) containing 0.5% (W/V) creatinine, 0.5% (W/V) yeast extract, 0.36% (W/V) potassium secondary phosphate, 0.04% (W/V) potassium primary phosphate, 0.02% (W/V) magnesium sulfate, 0.001% (W/V) manganese sulfate and 0.001% (W/V) iron sulfate was placed in a small size culture apparatus equipped with stirrer (manufactured by Iwashiya Co., Japan) and sterilized at a high pressure. Then, the medium was inoculated with 20 ml of a seed bacterial solution prepared by preculturing Flavobacterium U-188 (ATCC 31200, FERM-P No. 2922) in a nutrient medium having the same composition as above, and submitted to an aeration-agitation submerged culture at 30° C. After being cultured for 24 hours, there was obtained a culture solution containing 6.5 units/ml of creatinine amidohydrolase and 2.2 units/ml of creatine amidinohydrolase.

The culture solution was freed from bacteria by adding 15 ml of 23.6% (W/V) solution of manganese sulfate with stirring, further adding 15 g of Hyflow Super Cel and filtering the resulting mixture. Thus, 970 ml of crude enzyme solution containing 6.4 units/ml of creatinine amidohydrolase and 2.1 units/ml of creatine amidinohydrolase were obtained.

The crude enzyme solution thus obtained was concentrated to a volume of 95 ml by means of Diaflow concentrating apparatus (manufactured by Amicon Co., U.S.A.). The concentrate was dialyzed against 5 liters of 0.05 M phosphate buffer (pH 8.0) containing 1 millimole of 2-mercaptoethanol (hereinafter called as buffer A) for 24 hours, and then loaded on a column (2 x 30 cm) of DEAE-cellulose which has preliminarily been equilibrated with buffer A. The portion adsorbed to the column had an activity of creatinine amidohydrolase, while the unadsorbed portion had an activity of creatine amidinohydrolase. When the adsorbed portion was eluted with a linear gradient of NaCl from 0 to 0.5 M, creatinine amidohydrolase was eluted at a NaCl-concentration of 0.2 to 0.3 M. The specific activity of enzyme was 48 units/mg-protein and a total activity was 4966 units. Then, the combined active fractions were dialyzed against the above-mentioned buffer A, after which they were charged on a column of DEAE-Sephadex A-50 (1.4 x 40 cm) (manufactured by Pharmacia Co., Sweden) which had preliminarily been equilibrated with the above-mentioned buffer A and then eluted with a linear gradient of NaCl from 0 to 0.5 M, whereby creatinine amidohydrolase was eluted at a NaCl-concentration of 0.1 - 0.3 M. The active fractions of the eluate had a specific activity of 83 units/mg-protein and a total activity of 3970 units. Subsequently, the combined active fractions were concentrated by means of collodion bag to a volume of 2.0 ml. The concentrate was passed through a column packed with Sepharose 6B (2 x 108 cm) which had preliminarily been equilibrated with the above-mentioned buffer A, and eluted with the above-mentioned buffer A to collect the fractions having the activity of creatinine amidohydrolase. The fractions were concentrated and lyophilized to give a purified enzyme power of creatinine amidohydrolase.

The purified creatinine amidohydrolase thus obtained had a specific activity of 160 units/mg- protein, a total activity of 2500 units and the yield was 40.3%.

The unit of creatine amidohydrolase activity, herein referred to, is so defined that the quantity of enzyme necessary for decomposing 1 micromole of creatinine per one minute in phosphate buffer (pH 6.5) at 37° C to produce creatine is taken as one unit.

On the other hand, creatine and amidinohydrolase can be obtained by charging the unadsorbed portion obtained in the afore-mentioned DEAE-cellulose column chromatography on a DEAE-Sephadex A-50 column previously equilibrated with the same buffer A as above, eluting it with a linear gradient of NaCl from 0 to 0.5 M. Creatine amidinohydrolase was eluted at a NaCl concentration of 0.1 to 0.3 M. The active fraction of the eluate has a specific activity of 8.5 units/mg-protein and a total activity of 1530 units.

Subsequently, the above-mentioned active fraction was concentrated to a volume of 2.0 ml by means of collodion bag, and the concentrate was passed through a Sepharose 6B colume (2 x 108 cm) which had preliminarily been equilibrated with the same buffer A as above. Then, it was eluted with the same buffer and the fractions having the activity of creatine amidinohydrolase were collected. The fractions were concentrated and lyophilized to give a purified powder of creatine amidinohydrolase. The purified creatine amidinohydrolase thus obtained had a specific activity of 11.3 units/mg-protein and a total activity of 1050 units. The yield was 51.6%.

The unit of creatine amidinohydrolase activity herein referred to was so defined that the quantity of enzyme necessary for decomposing 1 micromole of creatine into urea per one minute in a phosphate buffer (pH 7.7) at 37° C is taken as one unit.

EXAMPLE 2

One liter of a nutrient medium (pH 7.6) containing 0.5% (W/V) creatine, 0.5% (W/V) yeast extract, 0.5% (W/V) polypeptone, 0.36% (W/V) potassium secondary phosphate, 0.04% (W/V) potassium primary phosphate, 0.02% (W/V) magnesium sulfate, 0.001% (W/V) manganese sulfate, and 0.001% (W/V) iron sulfate was placed in a culture flask of 5 liter capacity and sterilized at a high pressure while the flask was stoppered with cotton. The medium was inoculated with 10 ml of a seed bacterial solution of Micrococcus luteus ATCC 398 obtained by preculturing it for 24 hours in a nutrient medium having the same composition as above, after which it was cultured at 30° C while being shaken with Rotary Shaker. After being cultured with shaking for 24 hours, a crude enzyme solution containing creatinine amidohydrolase (0.5unit/1 ml of culture solution) and creatine amidinohydrolase (0.3 unit/1 ml of culture solution) was obtained.

The crude enzyme solution was treated in the same manner as in Example 1 to obtain pure creatinine amidohydrolase and creatine amidinohydrolase.

Example 3

One liter of a nutrient medium (pH 7.6) containing 0.5% (W/V) polypeptone, 0.5% (W/V) yeast extract, 0.36% (W/V) potassium secondary phosphate, 0.04% (W/V) potassium primary phosphate, 0.02% (W/V) magnesium sulfate, 0.001% (W/V) manganese sulfate, and 0.001% (W/V) iron sulfate was placed in a culture flask of 5 liter capacity and sterilized at a high pressure while the flask was stoppered with cotton. The medium was inoculated with 10 ml of a culture solution obtained by preculturing Corynebacterium U-41 (ATCC 31201, FERM-P No. 2923) for 24 hours in a nutrient medium having the same composition as above. The inoculated medium was cultured at 30° C with shaking. After culturing for 5 hours, 100 ml of sterilized 5% (W/V) creatinine solution was added to the medium and the culture was continued for an additional 24 hours, whereby a crude enzyme solution containing creatinine amidohydrolase (2.1 units/1 ml of culture solution) and creatine amidinohydrolase (0.5 unit/1 ml of culture solution) was obtained.

The crude enzyme solution was treated in the same manner as in Example 1 to obtain pure creatinine amidohydrolase and creatine amidinohydrolase.

What is claimed is:

1. Creatinine amidohydrolase of which $K_m$ value (Michaelis constant) for creatinine is $3.45 \times 10^{-2}$ moe (37° C, pH 6.5), $K_m$ value for creatine is $4.35 \times 10^{-2}$ mole (37° C, pH 6.5), stable pH range is 7.0 - 9.5, optimum pH is 6.5, action temperature range is 40° - 70° C, optimum action temperature is 65° C, and molecular weight is about 150,000.

2. Creatine amidinohydrolase of which $K_m$ value (Michaelis constant) for creatine is $4.0 \times 10^{-2}$ mole (37° C, pH 7.7), stable pH range is 5.9-9.0, optimum pH is 7.7, action temperature range is 20°-45° C, optimum action temperature is 37° C, and molecular weight is about 60,000 and is produced by a bacterial strain of Flavobacterium U-188 (ATCC 31200, FERM-P No. 2922), Corynebacterium U-41 (ATCC 31201, FERM-P No. 2923), or Micrococcus luteus (ATCC 398).

3. A process for preparing creatinine amidohydrolase and/or creatine amidinohydrolase characterized by culturing a bacterial strain of Flavobacterium U-188 (ATCC 31200, FERM-P No. 2922), Corynebacterium U-41 (ATCC 31201, FERM-P No. 2923) or Micrococcus luteus (ATCC 398) having an ability to produce creatinine amidohydrolase and creatine amidinohydrolase in a nutrient medium in the presence of creatinine, creatine or a mixture thereof and collecting creatinine amidohydrolase and/or creatine amidinohydrolase from the cultured fluid.

4. A process according to claim 3, wherein the nutrient medium contains at least one member selected from the group consisting of yeast extract, peptone, meat extract, corn steep liquor, and water extract of soy bean and wheat bran as a nitrogen source and at least one member selected from the group consisting of potassium primary phosphate, potassium secondary phosphate, magnesium sulfate, magnesium chloride, ferric chloride, ferric sulfate and maganese sulfate as an inorganic salt.

5. A process according to claim 3, wherein a sugar material or a vitamin is inocorporated into the nutrient medium.

6. A process according to claim 3, wherein the quantity of creatinine, creatine or a mixture thereof is in the range of 0.01 to 5.0% (W/V) based on the total nutrient medium.

7. A process according to claim 3, wherein the initial pH value of the nutrient medium is 7 to 9.

8. A process according to claim 3, wherein the culture is carried out at a temperature of 25° to 37° C.

9. A process according to claim 3, wherein the culture is carried out for 10 to 48 hours.

10. A process according to claim 3, wherein the culture is carried out with aeration by the method of aeration-agitation submerged culture or shaking culture.

11. A process according to claim 3, wherein the culture is carried out by inoculating a bacterial strain into a nutrient medium which has preliminarily been incorporated with creatinine, creatine or a mixture thereof.

12. A process according to claim 3, wherein creatinine, creatine or a mixture thereof is added to the nutrient medium at a time not later than 5 hours after the culture is started by inoculating a bacterial strain into the nutrient medium.

13. A process according to claim 3, wherein creatinine amidohydrolase or creatine amidinohydrolase is obtained in the form of a crude enzyme solution by separating and removing the cells and insoluble materials from the culture solution or it is obtained in the form of a crude enzyme powder by further lyophilizing said crude enzyme solution.

14. A process according to claim 13, wherein a pure creatinine amidohydrolase or creatine amidinohydrolase is obtained by purifying said crude enzyme solution or crude enzyme powder.

15. A process according to claim 14, wherein the purification is carried out by the adsorption-elution method by use of an ion exchange material.

16. A process according to claim 14, wherein the purification is carried out by combining the gel filtration method by use of Sephadex G-100, Sephadex G-200 or Sepharose 6B, the adsorption-elution method by use of hydroxyl apatite and the electrophoresis method by use of polyacrylamide gel.

* * * * *